(12) United States Patent
Sonntag

(10) Patent No.: US 7,131,440 B2
(45) Date of Patent: *Nov. 7, 2006

(54) INHALATION THERAPY APPARATUS HAVING A VALVE FOR LIMITING THE INSPIRATION FLOW

(75) Inventor: Uwe Sonntag, Pocking (DE)

(73) Assignee: Pari GmbH Spezialisten fur effektive Inhalation, Starnberg (DE)

( * ) Notice: Subject to any disclaimer, the term of this patent is extended or adjusted under 35 U.S.C. 154(b) by 412 days.

This patent is subject to a terminal disclaimer.

(21) Appl. No.: 10/159,964

(22) Filed: May 29, 2002

(65) Prior Publication Data
US 2003/0037785 A1 Feb. 27, 2003

(30) Foreign Application Priority Data
Jun. 1, 2001 (DE) .................................. 101 26 807

(51) Int. Cl.
*A61M 15/00* (2006.01)
*A61M 16/10* (2006.01)

(52) U.S. Cl. .............................. 128/203.12; 128/205.24

(58) Field of Classification Search ........... 128/200.14, 128/200.21, 200.25, 200.18, 203.12, 203.15, 128/205.24, 207.12, 207.16
See application file for complete search history.

(56) References Cited

U.S. PATENT DOCUMENTS

| 4,862,884 A | * | 9/1989 | Christianson | ........... 128/204.26 |
| 4,892,094 A | * | 1/1990 | Shigematsu | ............. 128/201.28 |
| 5,251,618 A | * | 10/1993 | Christianson | ........... 128/205.24 |
| 5,437,271 A | | 8/1995 | Hodson et al. | |
| 6,109,261 A | | 8/2000 | Clarke et al. | |

FOREIGN PATENT DOCUMENTS

| EP | 0 134 847 | 3/1985 |
| EP | 0 281 650 | 9/1988 |
| EP | 0 895 788 | 2/1999 |
| GB | 451537 | 8/1936 |

\* cited by examiner

*Primary Examiner*—Michael J. Hayes
*Assistant Examiner*—Michael G. Mendoza
(74) *Attorney, Agent, or Firm*—Merchant & Gould P.C.

(57) ABSTRACT

In an inhalation therapy apparatus a limiter section is provided in the air supply duct which serves as the limiting element for the movement of a valve element of an inlet valve. In the limiter section are provided openings through which surrounding air can flow when the valve element rests against the front edge of the limiter section facing the valve element.

14 Claims, 3 Drawing Sheets

INHALATION THERAPY APPARATUS HAVING A VALVE FOR LIMITING THE INSPIRATION FLOW

FIELD OF THE INVENTION

The present invention concerns an inhalation therapy apparatus and in particular a valve for limiting the inspiration flow in an inhalation therapy apparatus.

BACKGROUND OF THE INVENTION

From EP-B-0 281 650 is known an aerosol atomiser which consists of an essentially cylindrical main body in which is arranged an atomiser nozzle for atomising an aerosol and into which projects an air supply duct for the supply of the surrounding air. The external opening of the air supply duct is closed by an inlet valve which is constructed as a one-way valve. It allows the inflow of surrounding air into the nebuliser housing when a patient inhales through a mouth piece of the aerosol atomiser but prevents the aerosol from escaping from the internal chamber of the atomiser during pauses in the breathing and in the event of the patient breathing into the aerosol atomiser during exhalation. The known inhalation therapy apparatus accordingly is constructed in such a way that the patient can breathe in any desired volume of air, limited only by the flow resistance determined by the shape of the atomiser. This flow resistance as a rule is not however of any consequence to the inspiration flow of up to 100 l/min reached by a patient.

From EP-A-0 895 788 is known a valve for providing a freely predetermined limitation of the inspiration flow, so that the patient during inhalation can breathe in without any significant flow resistance only until reaching a maximum inspiration flow (threshold value) e.g. of approximately 30 l/min. On reaching or exceeding the threshold value, the movement of the valve element provided in the inlet valve is limited to such an extent that an increased flow resistance is set up. In the inhalation therapy apparatus according to the EP-A-0 895 768 this is achieved in that opposite to the valve element provided for closing the inhalation openings there is provided a limiting element against which the valve element rests when the inspiration flow of the patient exceeds the threshold value. The valve element then closes a large part of the openings which are present in the limiting element and permits the flowing through of the breathed in surrounding air only through very much smaller openings, thus increasing the flow resistance to the inhalation. The limiting element in the inhalation therapy apparatus according to the EP-A-0 895 788 is an additional component which has to be fitted in the vicinity of the valve element, especially after each cleaning process of the inlet valve by the patient.

With this prior art in the background it is the aim of this invention to further improve the known inhalation apparatus.

SUMMARY OF THE INVENTION

Achieved is this aim in that the invention proposes an embodiment which for the patient is easier to handle, as the separately to handle limiting element is made obsolete. Through the invention the patient is provided with an inhalation therapy apparatus which is improved with a view to handling.

As described in patent claim 1, the inhalation therapy apparatus according to the invention is characterised by the fact that the limiting element is attached to the air supply duct and preferably integrated with the same, in particular is constructed as a one-piece extension of the air supply duct in the direction of the valve element. Apart from that, the limiter section of the air supply duct has air inhalation openings through which, on exceeding the inspiration flow threshold value, the inhaled surrounding air substantially flows.

BRIEF DESCRIPTION OF THE DRAWINGS

Advantageous embodiments are disclosed in the sub-claims. The following embodiment example is described in more detail with the aid of drawings, these show:

DETAILED DESCRIPTION OF THE INVENTION

Figure 1:
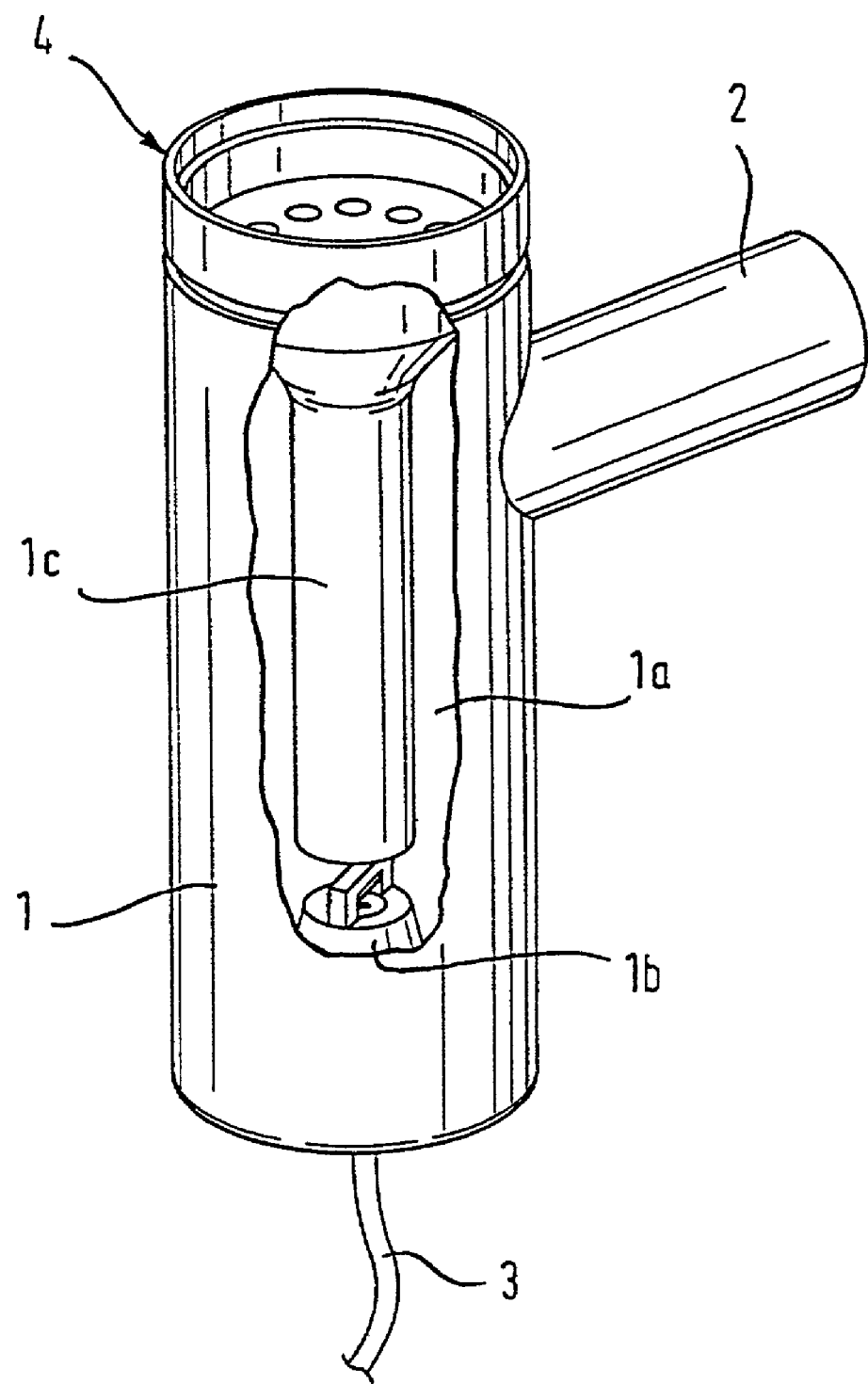
FIG. 1 an inhalation therapy apparatus with an inlet valve and a limiting element according to the invention.

In FIG. 1 is shown an inhalation therapy apparatus which consists of a cylindrical main body 1 and a connecting piece 2 formed thereto. Inside the cylindrical main body, i.e. in the nebuliser chamber 1a, is arranged an atomiser nozzle 1b (see for example EP-B-0 281 650) which produces an aerosol from a medicine stored in the inhalation therapy apparatus. For this the atomiser nozzle 1b is supplied with compressed air via a pressure medium pipe 3. In the connecting piece 2 is normally arranged a mouthpiece or mask through which the patient can breathe in the aerosol produced in the nebuliser chamber. From the top end of the cylindrical main body 1 in FIG. 1 a cylindrical air supply duct 1c projects into the nebuliser chamber. Through this air supply duct 1c the surrounding air can continue to flow into the interior 1a of the inhalation therapy apparatus when the patient breathes in the aerosol via the connecting piece 2. On the outward pointing opening of the air supply duct 1c is provided a passive inlet valve 4 which is constructed as a one-way valve and whose make-up is described in more detail in the following with reference to FIG. 2.

Figure 2A:
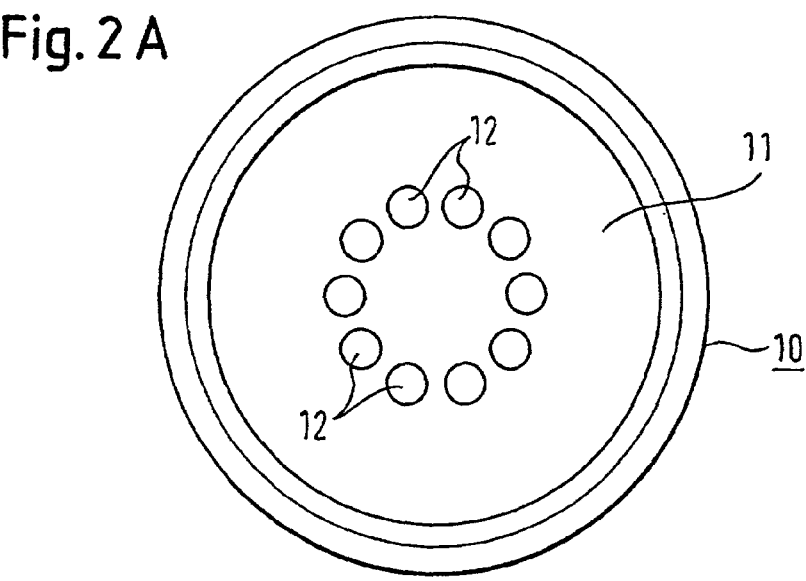
FIG. 2A–2C the inlet valve and limiting element according to the invention in various detailed views.
Figure 2B:
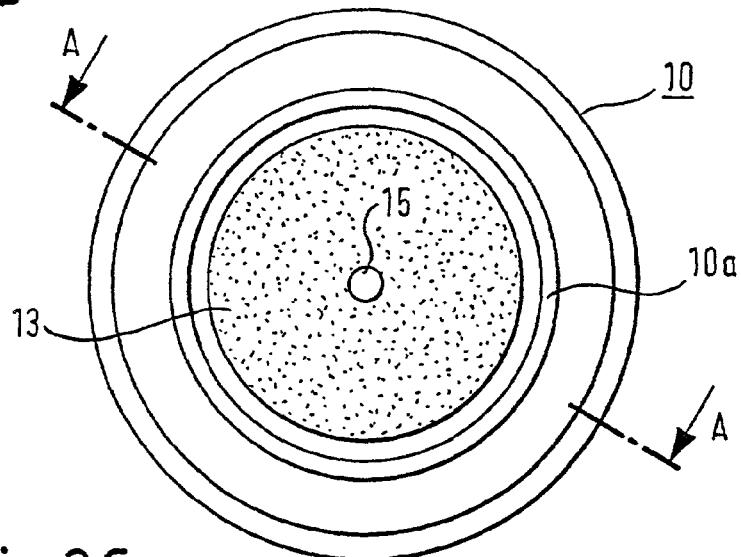
Figure 2C:
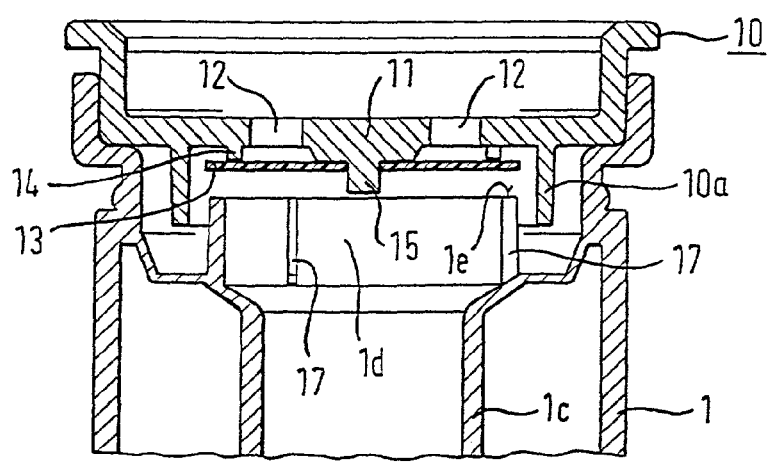

FIG. 2A shows the passive inlet valve 4 from the side facing outwards, i.e. from the side which can also be seen in FIG. 1. FIG. 2B shows the passive inlet valve 4 on the side facing the air supply duct which is not visible in FIG. 1. FIG. 2C shows a cross-section through the passive inlet valve 4 along the line A—A in FIG. 2B in a condition mounted in an inhalation therapy apparatus.

In FIG. 2A to FIG. 2C it can be seen that the passive inlet valve 4 of the here described embodiment example of the invention consists of a cylindrical main body 10 with a surface area formed in several steps and a closure wall 11 running perpendicular to the cylinder axis. In the closure wall 11 are provided a plurality of air inlet openings 12 which can also be described as through openings and through which surrounding air can flow into the interior of the inhalation therapy apparatus. In the cylinder section 10a with the smallest outer diameter is arranged a valve element 13 which has the form of a small circular valve plate with a central securing opening. The small valve plate 13 consists of an elastic material, for example silicon, with a sufficient inherent stiffness which in the non-deflected rest position allows the small valve plate 13 to shut the air inlet openings 12 of the limiting valve 4, at least when the patient exhales into the inhalation therapy apparatus. As shown in FIG. 2C, a continuous circular sealing lip 14 can be additionally provided on the side of the closure wall 11 facing the small valve plate. The small valve plate 13 for securing is mounted on a pin 15 extending along the cylinder axis on the side of the inlet valve 4 facing the interior chamber 1a of the inhalation therapy apparatus.

This construction functions as follows. When the patient inhales through the inhalation therapy apparatus, the small valve plate 13 is deflected inwards and thus allows additional air to flow through the air inlet openings 12 of the inlet valve 4. The opening cross-section thus created is substantially proportional to the underpressure built up in the nebuliser chamber. During pauses in breathing or at least during exhalation by the patient into the inhalation therapy apparatus, the valve element 13 shuts the openings 12.

As can be seen from FIG. 2C, according to the invention the air supply duct 1c at the end opposite the small valve plate 13 is constructed in such a way that it extends into the direct proximity of the small valve plate 13 and assumes the function of a limiting element. This means that the limiter section 1d of the air supply duct 1c limits the deflection of the small valve plate 13. The size of the small valve plate 13 is therefore selected to be such that it rests on the front edge 1e of the limiter section 1d of the air supply duct 1c when the inspiration flow, caused by the inhalation of the patient, exceeds a threshold value of for example approximately 30 l/min. For this the diameter of the valve element 13 is preferably larger but at least equal to the diameter of the limiter section 1d. The threshold value can be determined by the distance between the valve element and the edge 1e on the front side. The limiter section 1d of the air supply duct has air throughput openings 17 which are so arranged that a flow-through of the sucked in air can still be possible even when the valve element 13 rests on the edge 1e of the front side. However, the size of the air throughput openings 17 are selected in such a way that, when the valve element 13 rests on the front edge 1e of the limiter section 1d of the air supply duct 1c, a flow resistance is produced which the patient can sense. The size of the air throughput openings 17 also has an influence on the threshold value for the maximum inspiration flow.

So long as the patient inhales within the pressure/flow range which is desirable in an aerosol physical sense, for example an inspiration flow below 30 l/min, the flow resistance, which is opposed by the inhalation through the inhalation therapy apparatus, is low and hardly affects the inhalation process of the patient. If the inspiration flow increases over the given threshold value, i.e. if the patient does not breathe within a pressure/flow range which is not desirable in an aerosol physical sense, the the small valve plate 13 rests against the front edge 1e of the limiter section 1d of the air supply duct 1c, which causes the air supply duct to be closed on the front side and the inhaled surrounding air is forced to flow through the air throughput openings 17 in the limiter section 1d of the air supply duct 1c. The thus increased flow resistance which is clearly felt by the patient causes the patient to reduce the inspiration flow, so that it drops again below the threshold value, which leads to the valve element 13 being raised from the front edge 1e of the limiter section 1d of the air supply duct 1c. The embodiment of the inhalation therapy apparatus according to the invention finally has the effect that the patient breathes within the pressure/flow range which is desirable in the aerosol physical sense.

As already shown in FIG. 2C, the air throughput openings 17 are significantly smaller than the cross-section of the air supply duct 1c. The form of the air throughput openings 17 is arbitrary. In FIG. 2C are shown slot-like air throughput openings. The air throughput openings 17 may also be quadratic, semi-circular or triangular-shaped recesses which extend to the front edge 1e of the limiter section 1d of the air supply duct 1c. For forming the air throughput openings 17 the edge 1e may be constructed completely or partly in undulating or zigzag shape. However, the air throughput openings 17 may also be constructed in such a way that they do not extend to the edge 1e but may be constructed as openings in the limiter section 1d of the air supply duct 1c. The shape and the number in both cases may be selected in accordance with the application and demands of the inlet valve or the inhalation therapy apparatus.

Figure 3:
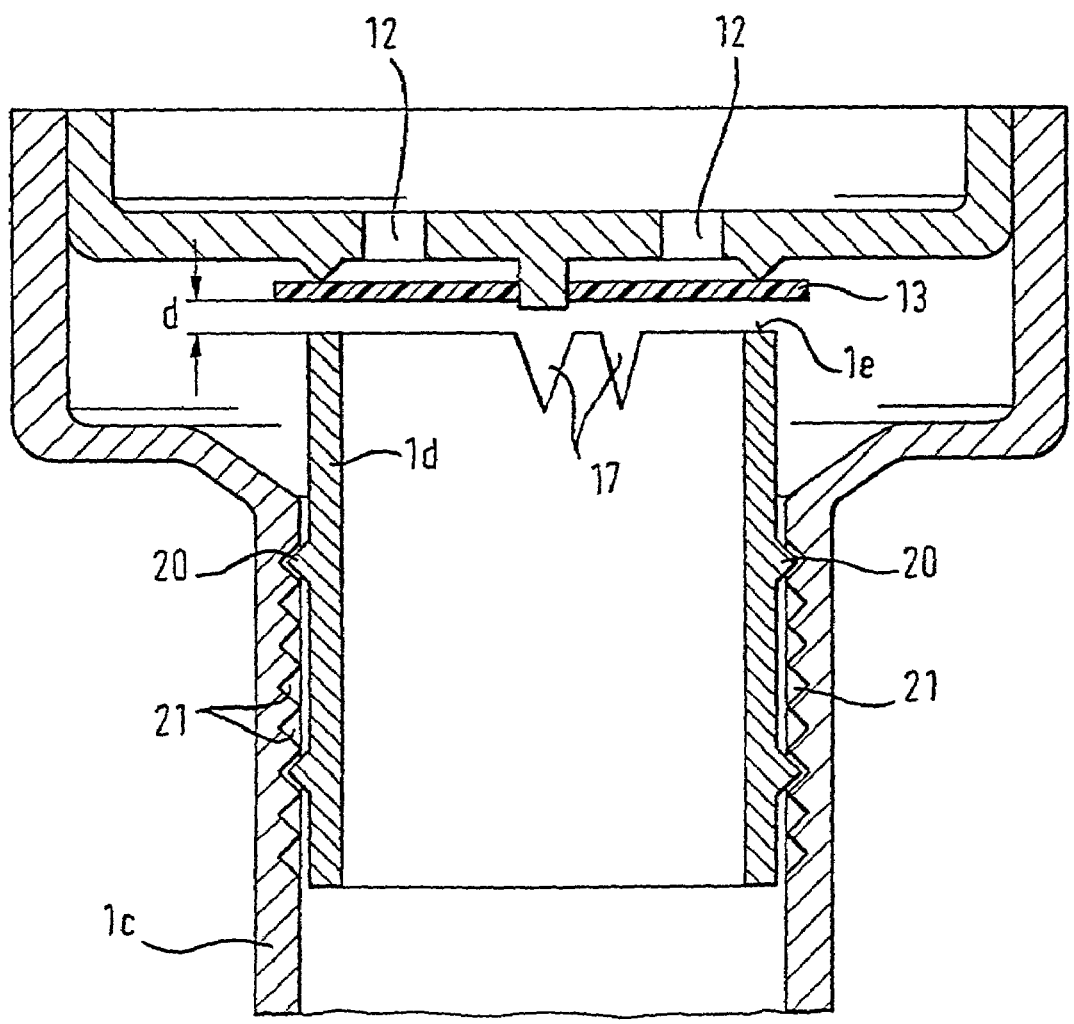
FIG. 3 a sectional view of the inlet valve and the limiting element according to the invention.

The limiter section 1d may, however, also be constructed as a separate part of the inhalation nebuliser according to the invention to be inserted into the air supply duct. Such an embodiment of the limiter section 1d of the air supply duct 1c is shown in FIG. 3. As can be seen in this figure, the limiter section 1d is constructed as a cylinder shell which in at least sections of its outer casing has snap-in projections 20 which can be snapped in to correspondingly shaped snap-in notches 21. The snap-in notches are constructed as continuous grooves running along the inner surface of the air supply duct 1c. In the example shown in FIG. 3 the grooves are wedge-shaped. The snap-in projections 20 on the limiter section 21 also can be constructed as continuously running snap-in projection. However, the construction must be such that the limiter section 1d can be inserted into the air supply duct 1c. However, this can be easily achieved by a corresponding dimensioning and shaping of the snap-in projections 20 in relation to the snap-in notches 21. The limiter section 1d can then be arranged in different snap-in positions in the air supply duct 1c. With the aid of the snap-in means it is therefore possible to flexibly adjust the distance d between the front edge 1e of the limiter section 1d and the valve element 13. The distance d however determines the threshold value at which the valve element 13 reaches the front edge 1e of the limiter section 1d and rests on it. In this embodiment example the valve element 13 has a larger diameter than the limiter section 1d.

In the embodiment example shown in FIG. 3 the air throughput openings 17 are wedge-like and extend to the edge 1e on the front side.

The inhalation therapy apparatus according to the invention is characterised by the fact that the limiter element is arranged in the air supply duct 1c, preferably constructed in one piece with the air supply duct. This has the effect that after removal of the inlet valve, easily to handle components of the inhalation therapy apparatus according to the invention are exposed. In particular the possibility of cleaning the inlet valve is significantly improved. The integral embodiment of the limiter section and the air supply duct reduces further the number of parts handled by the patient, which further simplifies the handling of the inhalation therapy apparatus according to the invention.

The invention claimed is:

1. Inhalation therapy apparatus comprising:
   a nebuliser chamber in which with the aid of an atomizer nozzle an aerosol is produced,
   a connecting piece through which the aerosol is discharged from the nebuliser chamber,
   an air supply duct through which the surrounding air enters the nebuliser chamber, and
   an inlet valve which is arranged at one end of the air supply duct and which comprises at least one inlet opening and one valve element closing the inlet opening and which is arranged in the air supply duct in such a way that an underpressure in the nebuliser chamber moves the valve element in order to free the inlet opening, wherein the air supply duct is provided with a limiter section which restricts the movement of the valve element in such a way that the freeing of the inlet opening is essentially proportional to the underpressure only up to a threshold value of the underpressure in the nebuliser chamber, and the limiter section is constructed to be connected to the air supply duct.

2. Inhalation therapy apparatus according to claim 1, wherein the limiter section can be inserted into the air supply duct.

3. Inhalation therapy apparatus according to claim 2, wherein the limiter section has snap-in projections which in the snap-in condition engage with snap-in notches in the air supply duct.

4. Inhalation therapy apparatus according to claim 3, wherein the snap-in projections and the snap-in notches are constructed in such a way that the distance between an edge of the limiter section facing the valve element and the valve element can be adjusted.

5. Inhalation therapy apparatus according to claim 1, wherein the limiter section has openings.

6. Inhalation therapy apparatus according to claim 5, wherein the openings extend up to an edge facing the valve element, of the limiter section of the air supply duct.

7. Inhalation therapy apparatus according to claim 1, wherein the limiter section of the air supply duct is constructed in such a way that the valve element does not rest against an edge of the limiter section of the air supply duct until a freely adjustable maximum inspiration flow of about 20 to 40 l/min is achieved.

8. Inhalation therapy apparatus according to claim 1, wherein the limiter section has a cylindrical basic shape which substantially corresponds to the cylindrical form of the air supply duct.

9. Inhalation therapy apparatus according to claim 8, wherein the diameter of the limiter section of the air supply duct is substantially equal to the diameter of the air supply duct.

10. Inhalation therapy apparatus according to claim 1, wherein the valve element comprises an elastic element.

11. Inhalation therapy apparatus according to claim 1, wherein the diameter of the valve element is bigger than the diameter of the limiter section.

12. Inhalation therapy apparatus according to claim 7, wherein the limiter section of the air supply duct is constructed in such a way that the valve element does not rest against the edge of the limiter section of the air supply duct until a freely adjustable maximum inspiration flow of about 30 l/min is achieved.

13. Inhalation therapy apparatus according to claim 10, wherein the valve element comprises silicon.

14. Inhalation therapy apparatus according to claim 1, wherein the limiter section is constructed to be integrally formed with the air supply duct.

* * * * *

UNITED STATES PATENT AND TRADEMARK OFFICE
CERTIFICATE OF CORRECTION

PATENT NO. : 7,131,440 B2
APPLICATION NO. : 10/159964
DATED : November 7, 2006
INVENTOR(S) : Sonntag It is certified that error appears in the above-identified patent and that said Letters Patent is hereby corrected as shown below:

Title page, (56) References Cited, U.S. Patent Documents: insert the following omitted U.S. Patents in appropriate order

| | | |
|---|---|---|
| --6,176,237 | 01/2001 | Wunderlich et al. |
| 5,349,947 | 09/1994 | Newhouse et al. |
| 4,741,331 | 05/1988 | Wunderlich |
| 4,333,450 | 06/1982 | Lester |
| 4,462,397 | 07/1984 | Suzuki |
| 3,769,973 | 11/1973 | Esbenshade, Jr. |
| 4,263,907 | 04/1981 | Lindsey |
| 4,454,877 | 06/1984 | Miller et al. |
| 6,258,170 | 07/2001 | Somekh et al. |
| 3,826,255 | 07/1974 | Havstad et al. |
| 3,874,379 | 04/1975 | Enfield et al. |
| 4,093,124 | 06/1978 | Morane et al. |
| 4,101,611 | 07/1978 | Williams |
| 4,198,969 | 04/1980 | Virag |
| 4,200,093 | 04/1980 | Camp |
| 4,225,542 | 09/1980 | Wall et al. |
| 4,231,973 | 11/1980 | Young et al. |
| 4,703,753 | 11/1987 | Bordoni et al. |
| 4,776,990 | 10/1988 | Verity |
| 4,805,609 | 02/1989 | Roberts et al. |
| 5,937,857 | 08/1999 | Caterini et al. |
| 5,937,850 | 08/1999 | Kawashima et al. |
| 5,738,087 | 04/1998 | King |
| 5,704,348 | 01/1998 | Drews |
| 5,584,288 | 12/1996 | Baldwin |
| 5,584,285 | 12/1996 | Salter et al. |
| 4,838,262 | 06/1989 | Katz |
| 4,210,174 | 07/1980 | Eross |

UNITED STATES PATENT AND TRADEMARK OFFICE
CERTIFICATE OF CORRECTION

PATENT NO.       : 7,131,440 B2
APPLICATION NO.  : 10/159964
DATED            : November 7, 2006
INVENTOR(S)      : Sonntag It is certified that error appears in the above-identified patent and that said Letters Patent is hereby corrected as shown below:

4,007,758    02/1977    Gray et al.--

Signed and Sealed this

Twenty-first Day of October, 2008

JON W. DUDAS
*Director of the United States Patent and Trademark Office*